United States Patent
Vartolone

(10) Patent No.: US 10,888,285 B2
(45) Date of Patent: Jan. 12, 2021

(54) IMAGING SYSTEM MAGNIFICATION STAND

(71) Applicant: HOLOGIC, INC., Marlborough, MA (US)

(72) Inventor: Joseph Vartolone, Danbury, CT (US)

(73) Assignee: Hologic, Inc., Marlborough, MA (US)

( * ) Notice: Subject to any disclaimer, the term of this patent is extended or adjusted under 35 U.S.C. 154(b) by 0 days.

(21) Appl. No.: 16/248,425

(22) Filed: Jan. 15, 2019

(65) Prior Publication Data

US 2019/0216412 A1     Jul. 18, 2019

Related U.S. Application Data

(60) Provisional application No. 62/617,408, filed on Jan. 15, 2018.

(51) Int. Cl.
    *A61B 6/04*     (2006.01)
    *A61B 6/02*     (2006.01)
    (Continued)

(52) U.S. Cl.
CPC ............ *A61B 6/0487* (2020.08); *A61B 6/00* (2013.01); *A61B 6/02* (2013.01); *A61B 6/025* (2013.01);
(Continued)

(58) Field of Classification Search
CPC .......... A61B 6/0457; A61B 6/00; A61B 6/02; A61B 6/025; A61B 6/04; A61B 6/0414;
(Continued)

(56) References Cited

U.S. PATENT DOCUMENTS

| 4,599,738 A | 7/1986 | Panetta et al. |
| 5,219,351 A | 6/1993 | Teubner et al. |

(Continued)

FOREIGN PATENT DOCUMENTS

| DE | 102006002905 A1 | 8/2007 |
| WO | 9317620 A1 | 9/1993 |

(Continued)

OTHER PUBLICATIONS

Communication pursuant to Article 94(3) EPC, for Application No. EP10707751.3, dated Aug. 7, 2019, 6 pages.
(Continued)

*Primary Examiner* — Courtney D Thomas
(74) *Attorney, Agent, or Firm* — Merchant & Gould P.C.

(57) ABSTRACT

An imaging system with integrated magnification stand is described. In an embodiment, the imaging system may include an imaging detector configured to capture an image of human tissue. The imaging system may include a compression paddle situated apart from the imaging detector. A magnification stand of the imaging system may be configured to rotate between a first position and a second position, wherein the magnification stand is situated between the compression paddle and the imaging detector in the first position such that the human tissue can be compressed between the magnification stand and the compression paddle, and wherein the magnification stand is rotated to the second position in which the second position is generally perpendicular to the first position. In this manner, the magnification stand may be stored on the imaging system itself. Other embodiments are described and claimed.

19 Claims, 13 Drawing Sheets

(51) Int. Cl.
*A61B 6/00* (2006.01)
*H04N 5/32* (2006.01)
*H04N 5/232* (2006.01)

(52) U.S. Cl.
CPC .............. *A61B 6/04* (2013.01); *A61B 6/0414* (2013.01); *A61B 6/467* (2013.01); *A61B 6/502* (2013.01); *A61B 6/589* (2013.01); *H04N 5/232* (2013.01); *H04N 5/232933* (2018.08); *H04N 5/32* (2013.01)

(58) Field of Classification Search
CPC ......... A61B 6/467; A61B 6/502; A61B 6/589; H04N 5/23933; H04N 5/232; H04N 5/32
USPC ...................................... 378/37, 62
See application file for complete search history.

(56) References Cited

U.S. PATENT DOCUMENTS

| | | | |
|---|---|---|---|
| 5,594,769 | A | 1/1997 | Pellegrino et al. |
| 6,765,985 | B2 | 7/2004 | Marie et al. |
| 2004/0170310 | A1* | 9/2004 | Kurahashi ............. A61B 6/484 382/128 |
| 2005/0084062 | A1 | 4/2005 | Andreasson et al. |
| 2005/0089205 | A1 | 4/2005 | Kapur et al. |
| 2006/0257009 | A1 | 11/2006 | Wang et al. |
| 2007/0076844 | A1* | 4/2007 | Defreitas ............. A61B 6/0414 378/37 |
| 2008/0198966 | A1 | 8/2008 | Hjarn et al. |
| 2009/0143674 | A1 | 6/2009 | Nields et al. |
| 2015/0269766 | A1 | 9/2015 | Kobayashi |
| 2017/0020473 | A1 | 1/2017 | Klausz et al. |

FOREIGN PATENT DOCUMENTS

| | | |
|---|---|---|
| WO | 9406352 A1 | 3/1994 |
| WO | 0051484 A2 | 9/2000 |
| WO | 2008014670 A1 | 2/2008 |

OTHER PUBLICATIONS

Extended European Search Report for Application No. EP19151689.7, dated Jul. 19, 2019, 12 pages.

* cited by examiner

800

IMAGING SYSTEM MAGNIFICATION STAND

CROSS-REFERENCE TO RELATED APPLICATION

This application claims priority to U.S. Provisional Patent Application No. 62/617,408, filed on Jan. 15, 2018, entitled "Automated and Configurable Magnification Stand," the contents of which are incorporated herein by reference.

TECHNICAL FIELD

Embodiments described herein generally relate to magnification stand configurations, and more particularly, to mammography or tomosynthesis image acquisition systems configured with a magnification stand is integrated into the system.

BACKGROUND

Mammography or tomosynthesis image acquisition systems may include various accessories that can be added to the system during a procedure. One such accessory is a magnification stand, which is a shelf-like device that is used to elevate tissue to be closer to an imaging source, creating a magnification effect in a resulting image. Magnification stands are conventionally manually adjusted and/or positioned to be placed among a plurality of hook mechanisms to adjust the level of magnification. Magnification stands need to be stored within an imaging suite and, when needed, physically hooked onto an imaging system. Storage space within imaging suites may be limited in some cases, and magnification stands typically take up considerable storage space. Further, it can be time consuming for practitioners to manually adjust among the various magnification levels and make corresponding adjustments in the imaging system while a patient is waiting for the image acquisition. Typically, magnification stands are utilized for diagnostic work-ups, for example, if follow up is needed after a screening examination or based on prior medical history. For at least these reasons, there is a need for improved techniques for storage and deployment of magnification stands in imaging systems, which would help with efficiency of workflow and throughput of patient examination and perhaps to help to reduce patient anxiety.

SUMMARY

The following presents a simplified summary in order to provide a basic understanding of some novel embodiments described herein. This summary is not an extensive overview, and it is not intended to identify key/critical elements or to delineate the scope thereof. Its sole purpose is to present some concepts in a simplified form as a prelude to the more detailed description that is presented later.

An imaging system with integrated magnification stand is described. In an embodiment, an imaging system may include an imaging detector to capture an image of human tissue. The imaging system may also include a compression paddle situated apart from the imaging detector. A magnification stand may be included and situated in a first position between the compression paddle and the imaging detector to compress the human tissue between the magnification stand and the compression paddle. A bottom portion of the magnification stand may be connected to the imaging system via a hinge configured to stow the magnification stand in a second position perpendicular, or substantially or generally perpendicular, to the first position. In this manner, the magnification stand may be stored on the imaging system itself. In an embodiment, the imaging system may include a position sensor configured to detect a position of the magnification stand. A processing circuit of the imaging system may configure a graphical user interface of the imaging system based upon a position detected by the position sensor. Other embodiments are described and claimed.

To the accomplishment of the foregoing and related ends, certain illustrative aspects are described herein in connection with the following description and the annexed drawings. These aspects are indicative of the various ways in which the principles disclosed herein can be practiced and all aspects and equivalents thereof are intended to be within the scope of the claimed subject matter. Other advantages and novel features will become apparent from the following detailed description when considered in conjunction with the drawings.

DETAILED DESCRIPTION

Figure 1:
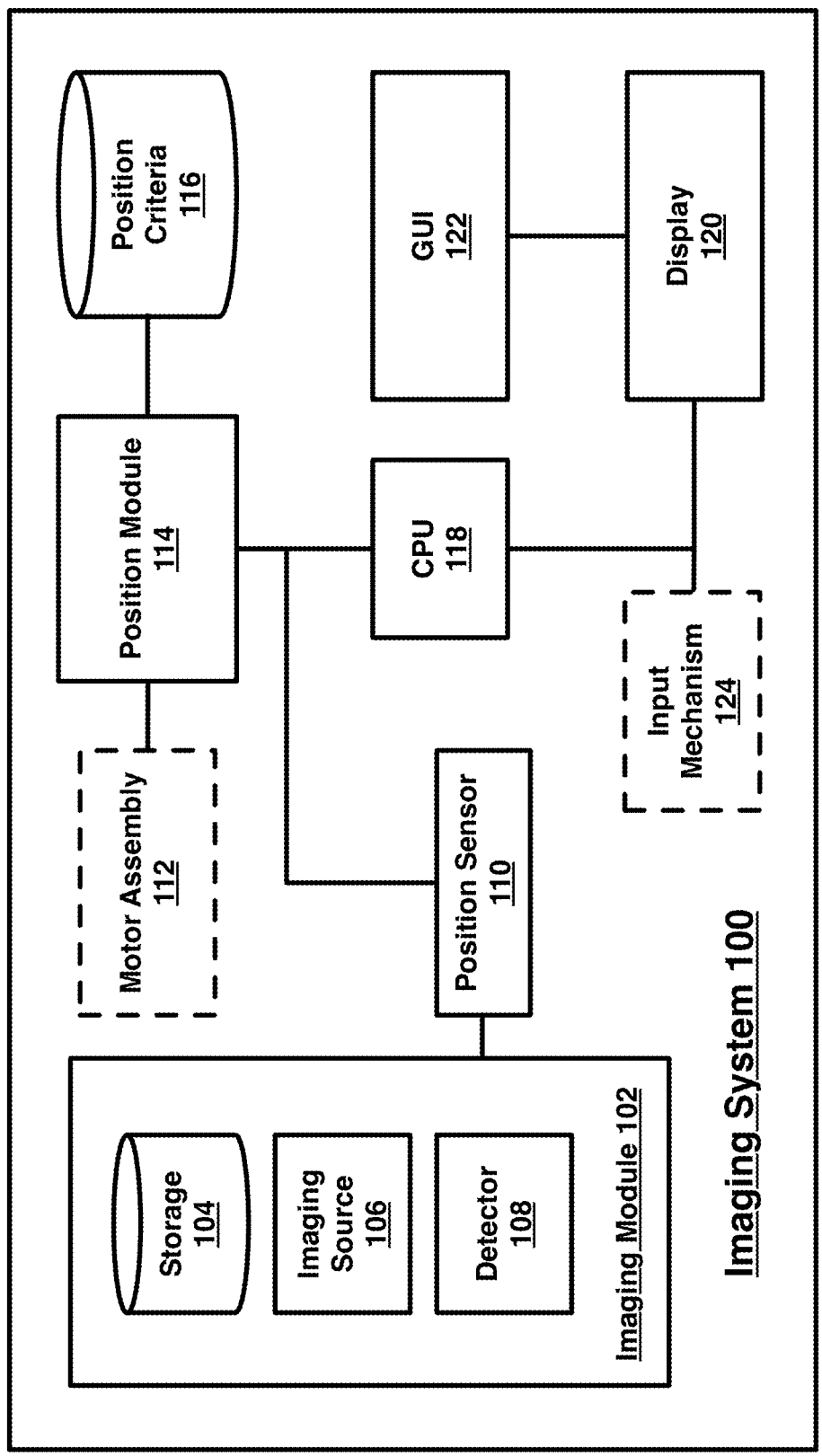
FIG. 1 illustrates an embodiment of an imaging system.

An imaging system having an integrated accessory, such as a magnification stand, is described. In an embodiment, an imaging system may include an imaging detector to capture an image of human tissue. The imaging system may optionally include a compression paddle situated apart from the imaging detector. A magnification stand may be included and situated in a first position between the compression paddle and the imaging detector to compress the human tissue between the magnification stand and the compression paddle. A bottom portion of the magnification stand may be connected to the imaging system via a rotational mechanism, such as a hinge, configured to stow the magnification stand in a second position different than that of a first position. In an embodiment, the second position is perpendicular or substantially perpendicular to the first position. In this manner, the magnification stand may be stored on or within the imaging system itself. In an embodiment, the imaging system may include one or more position sensors configured to detect a position of the magnification stand and/or a position of the compression paddle. A processing circuit of the imaging system may configure a graphical user interface of the imaging system based upon a position detected by the position sensor. Other embodiments are described and claimed.

With general reference to notations and nomenclature used herein, the detailed descriptions which follow may be presented in terms of program procedures executed on a computer or network of computers. These procedural descriptions and representations are used by those skilled in the art to most effectively convey the substance of their work to others skilled in the art.

A procedure is here, and generally, conceived to be a self-consistent sequence of operations leading to a desired result. These operations are those requiring physical manipulations of physical quantities. Usually, though not necessarily, these quantities take the form of electrical, magnetic or optical signals capable of being stored, transferred, combined, compared, and otherwise manipulated. It proves convenient at times, principally for reasons of common usage, to refer to these signals as bits, values, elements, symbols, characters, terms, numbers, or the like. It should be noted, however, that all of these and similar terms are to be associated with the appropriate physical quantities and are merely convenient labels applied to those quantities.

Further, the manipulations performed are often referred to in terms, such as adding or comparing, which are commonly associated with mental operations performed by a human operator. No such capability of a human operator is necessary, or desirable in most cases, in any of the operations described herein which form part of one or more embodiments. Rather, the operations are machine operations. Useful machines for performing operations of various embodiments include general purpose digital computers or similar devices.

Various embodiments also relate to apparatus or systems for performing these operations. This apparatus may be specially constructed for the required purpose or it may comprise a general-purpose computer as selectively activated or reconfigured by a computer program stored in the computer. The procedures presented herein are not inherently related to a particular computer or other apparatus. Various general-purpose machines may be used with programs written in accordance with the teachings herein, or it may prove convenient to construct more specialized apparatus to perform the required method steps. The required structure for a variety of these machines will appear from the description given.

FIG. 1 illustrates a block diagram for an imaging system 100. In one embodiment, the imaging system 100 may comprise one or more components. Although the imaging system 100 shown in FIG. 1 has a limited number of elements in a certain topology, it may be appreciated that the imaging system 100 may include more or less elements in alternate topologies as desired for a given implementation.

The imaging system 100 may include a plurality of modules, including imaging module 102, position sensor 110, and position module 114, which may each include one or more processing units, storage units, network interfaces, or other hardware and software elements described in more detail herein. In some embodiments, these modules may be included within a single imaging device, utilizing CPU 118. In other embodiments, one or more modules may be part of a distributed architecture.

In an embodiment, each module of imaging system 100 may include, without limitation, an imaging system, mobile computing device, a smart phone, a workstation, or a desktop computer, or other devices described herein. In various embodiments, imaging system 100 may comprise or implement multiple components or modules. As used herein the terms "component" and "module" are intended to refer to computer-related entities, comprising either hardware, a combination of hardware and software, software, or software in execution. For example, a component and/or module can be implemented as a process running on a processor, such as CPU 120, a hard disk drive, multiple storage drives (of optical and/or magnetic storage medium), an object, an executable, a thread of execution, a program, and/or a computer. By way of illustration, both an application running on a server and the server can be a component and/or module. One or more components and/or modules can reside within a process and/or thread of execution, and a component and/or module can be localized on one computer and/or distributed between two or more computers as desired for a given implementation. The embodiments are not limited in this context.

The various devices within system 100, and components and/or modules within a device of system 100, may be communicatively coupled via various types of communications media as indicated by various lines or arrows. In various embodiments, the various modules and storages of system 100 may be organized as a distributed system. A distributed system typically comprises multiple autonomous computers that communicate through a computer network. It is worthy to note that although some embodiments may utilize a distributed system when describing various enhanced techniques for data retrieval, it may be appreciated that the enhanced techniques for data retrieval may be implemented by a single computing device as well. The embodiments are not limited in this context.

In an embodiment, imaging module 102 may include an imaging source 106 and a detector 108, which may be used to perform breast imaging (2D digital mammography, tomosynthesis, molecular imaging, computed tomography, ultrasound or any combination thereof), and may be an x-ray source and detector in some examples. In other examples, imaging source 106 and detector 108 may be other types of imaging sources and sensors, respectively. For example, in some embodiments imaging module 102 may be configured to perform breast imaging, such as x-ray mammography, tomosynthesis, computed tomography, molecular imaging, and/or ultrasound. Tomosynthesis is a method for performing high-resolution limited-angle tomography at radiographic dose levels. While mammography is used as an exemplary embodiment through the description, it can be appreciated that the techniques described herein may be applicable to other procedures in which imaging of human tissue susceptible to movement may occur.

Imaging source 106 may be configured to expose human tissue, such as breast tissue, to x-rays, which may be detected by detector 108. Detector 108 may be configured to respond to the fluence of incident x-rays over a wide range. Detector 108 may be configured to absorb x-rays, produce an electronic signal, digitize the signal, and store the results in storage 104. The output image may be saved as a two-dimensional matrix, where each element represents the x-ray transmission corresponding to a path through the breast tissue. Three-dimensional images and matrices may be generated in some embodiments, depending on the imaging modality, such as tomosynthesis, computed tomography, and the like. The image may be digitally processed such that when it is displayed on a display device or printed on laser film, it will illustrate the key features required for diagnosis. Such diagnostic images may be stored in storage 104 so that they may be viewed on a user interface of display 120.

Imaging system 100 may include a position sensor 110, which may be arranged adjacent to or, at least partially, within a magnification stand, a hinge of a magnification stand, or within the body of an imaging system in proximity to a magnification stand. Position sensor 110 may be configured to determine when a magnification stand has been deployed, and may also determine the vertical position of the magnification stand after deployment. In an embodiment, position sensor 110 and/or an additional position sensor(s) may be configured to detect a position of the compression paddle. In this manner, logic executed by a processor or other circuitry may ensure that the compression paddle is properly placed above the magnification stand before it is deployed into a field of view.

Figure 2:
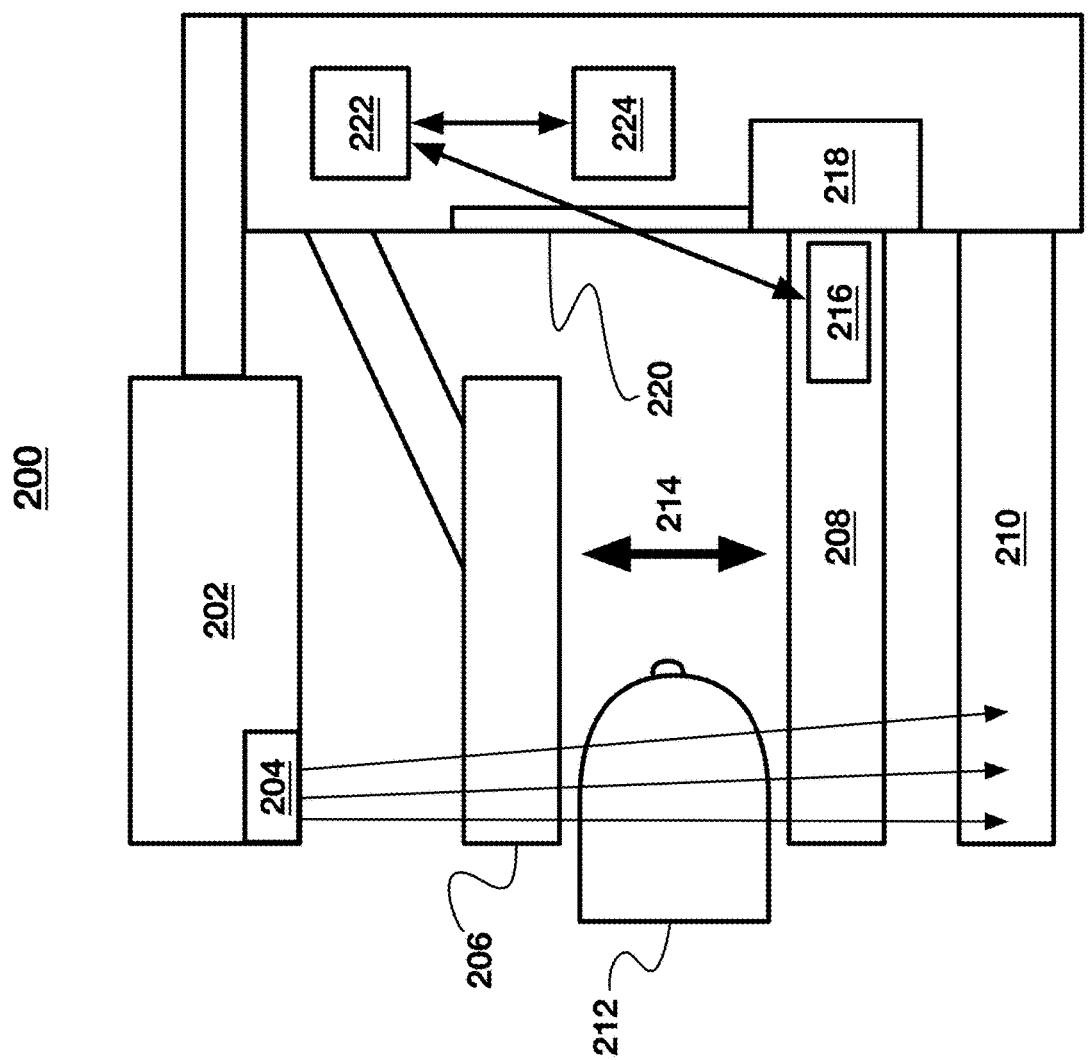
FIG. 2 illustrates an embodiment of an imaging system.

In some embodiments, position sensor 110 may be used in conjunction with motor assembly 112 to automatically deploy and vertically position the magnification stand based upon input from GUI 122 and/or input mechanism 124. As described herein, a magnification stand may be stowed on, partially within, or within the body of an imaging system. The magnification stand, when deployed, may be arranged to be generally parallel to a compression paddle of imaging system 100 and between the compression paddle and detector 108, positioning the subject tissue closer to imaging source 106. Once deployed, and as illustrated and described herein, a magnification stand may be configured into one or more vertical positions corresponding to different focal spots or magnification levels. In this manner, tissue compressed between the compression paddle and magnification stand may appear to be magnified in a resulting image (the magnification stand and compression paddle are not shown in FIG. 1, but are illustrated in FIG. 2, described below).

Position sensor 110 may include one or more devices capable of measuring the position of a magnification stand, and may include an absolute position sensor and/or a relative displacement sensor in some embodiments. Non-limiting examples of position sensor 110 include a capacitive transducer, a capacitive displacement sensor, an eddy-current sensor, an ultrasonic sensor, a grating sensor, a hall effect sensor, an inductive non-contact position sensors, an optical laser doppler vibrometer, a linear variable differential transformer (LVDT), a multi-axis displacement transducer, a photodiode array, a piezo-electric transducer (piezo-electric), a potentiometer, an optical proximity sensor, an angular rotary encoder, a seismic displacement pick-up, and or a string potentiometer (also known as string pot, string encoder, or cable position transducer). It can be appreciated that one or more, or any combination, of the above position sensors may be used to determine that a magnification stand has been deployed and the vertical position thereof.

The output of position sensor 110 may be an electrical signal representative of a deployment status (i.e., deployed or not deployed) and/or a level of vertical position. The output of position sensor 110 may be shared with position module 114. Position module 114 may be used in various embodiments either to automatically deploy a magnification stand into a selected position, or to detect a manual deployment and position of a magnification stand. In some embodiments, the magnification stand may be situated on a mechanical track, which may be manually or automatically positioned, for example, via a user interface comprising a GUI or other inputs, along the track.

In an embodiment, a magnification stand position may be input by a practitioner using a GUI 122 and/or input mechanism 124. GUI 122 may be displayed on display 120 and may include one or more options for deployment of a magnification stand. The magnification stand position may be automatically determined, for example, when a practitioner or technician has entered a magnification mode in the system. In an example, a plurality of magnification levels may be displayed, and may be selected by a practitioner. In another example, a plurality of focal spots may be displayed. A focal spot, as described herein, may include the area of the anode surface (detector) which receives the beam of electrons from the cathode (imaging source). For example, the size and shape of the focal spot may be determined by the size and shape of an electron beam when it strikes an anode. The size and shape of the electron beam may be determined by, among other factors, the position of a magnification stand. Thus, GUI 122 may provide a plurality of focal spots for selection, including, without limitation, 0.3 mm and 0.6 mm focal spots. A selection may be sent to position module 114. A position criteria database 116 may store correlations between focal spots and positions. For example, a particular focal spot selection may correspond with a particular vertical height for a magnification stand. Based upon position criteria 116, position module 114 may control motor assembly 112 to deploy a magnification stand into the selected position.

In an embodiment, position sensor 110 may be configured to detect manual deployment of a magnification stand. For example, a practitioner may manually deploy a magnification stand from a first, stowed, position to a second, deployed, position. The deployed position may be parallel to, and between, a compression paddle and image detector. A practitioner may also select a vertical position for the magnification stand, which may correspond to a focal spot or magnification level. Position sensor 110 may be configured to detect both deployment and vertical position and communicate the detected deployment and vertical position to position module 114. Position module 114 may be configured to correlate the received values from position sensor 110 using position criteria 116 and configure GUI 122 to display a parameter, such as a focal point or magnification level, that corresponds to the vertical position of the manually deployed magnification stand.

While the embodiments described above utilize GUI 122 displayed on display device 120, in an alternative embodiment, an input mechanism 124 may be use instead of GUI 122. For example, input mechanism 124 may include one or more mechanical or digital switches or buttons. Input mechanism 124 may allow a practitioner to deploy a magnification stand and/or select a particular vertical position. Further, input mechanism may include one or more LED lights, or other indicators, which may be labeled to indicate certain parameters, such as focal spot or magnification levels, to a practitioner.

FIG. 2 illustrates an imaging system 200 according to an embodiment. Imaging system 200 illustrates exemplary components most relevant to the techniques described herein and may include other components not depicted within FIG. 2. Upper portion 202 including imaging source 204, which may be an x-ray source in some embodiments and may be consistent with imaging source 106, described above with respect to FIG. 1.

Compression paddle 206 may be mounted to an arm, itself connected to a frame connected to a body of the imaging system 200. Compression paddle 206 may be lowered onto human tissue during an imaging procedure. Certain imaging procedures, such as mammography, may require compression of human tissue between compression paddle 206 and another surface, such as the surface of detector 210, which may be consistent with detector 108, described above with respect to FIG. 1. A magnification stand 208 may be deployed parallel to compression paddle 206 and detector 210, and may be position between them such that human tissue may be compressed at a distance 214, which is closer to imaging source 204. As described above, magnification of the subject tissue may be achieved by positioning human tissue 212 closer to imaging source 204.

A position sensor 216 may be included adjacent to or, at least partially, within the magnification stand, as illustrated, or in other embodiments, may be located adjacent to or, at least partially, within the body of imaging system 200. Position sensor may communication with position module 222, which in turn communicates with interface 224. Position module 222 may be consistent with position module 114, described with respect to FIG. 1. Interface 224 may be consistent with either the combination of display 120 and GUI 122, or may be consistent with input mechanism 124, both described within respect to FIG. 1.

Also illustrated within FIG. 2 is motor assembly 218 and vertical channel 220. Motor assembly 218 may be located adjacent to or, at least partially, within the body of imaging system 200, and may be configured to deploy magnification stand 208 into a position parallel to compression paddle 206 and detector 210. Deployment of magnification stand 208 may be performed using mechanism, such as a hinge mechanism, that allows magnification stand 208 to move from a first, stowed position to a second, deployed position. Further, motor assembly 218 may be configured to vertically position magnification stand 208 at one of a plurality of vertical positions within vertical channel 220.

Figure 3:
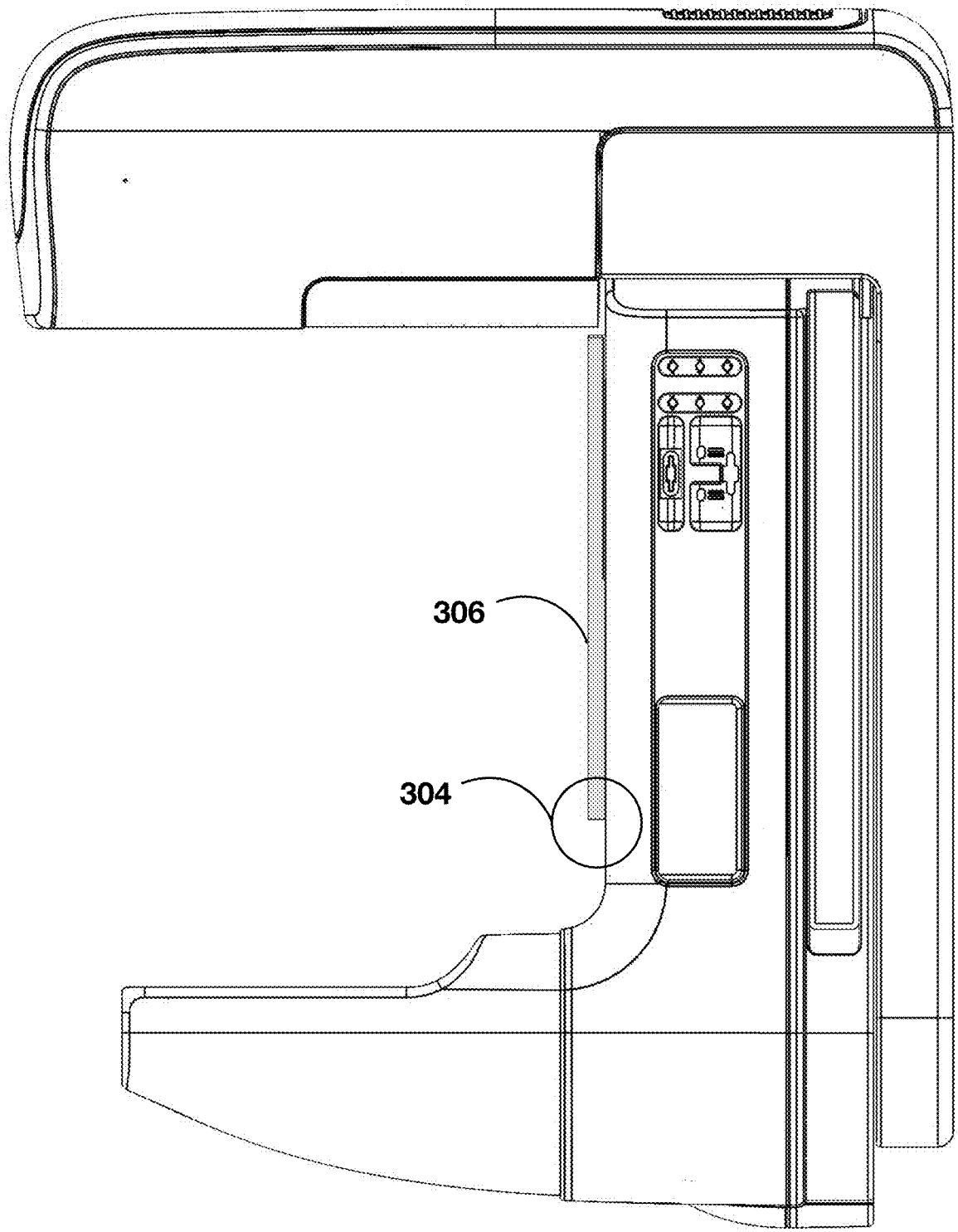
FIG. 3 illustrates an embodiment of an imaging system.

FIG. 3 illustrates an imaging system 300 according to an embodiment. As illustrated within FIG. 3, a magnification stand 306 may be stowed in an upright position via a hinge 304. In some embodiments, magnification stand 306 may be stowed, at least partially, within a recess or on the surface or, at least partially, within a mating surface corresponding in shape to the magnification stand when in the stowed position. In this manner, magnification stand 306 may be attached or otherwise integrated to imaging system 300, removing the need to separately store the magnification stand elsewhere within an imaging suite. Moreover, magnification stand 306 may be deployed, via hinge 304, into a deployed position either manually or automatically.

Figure 4:
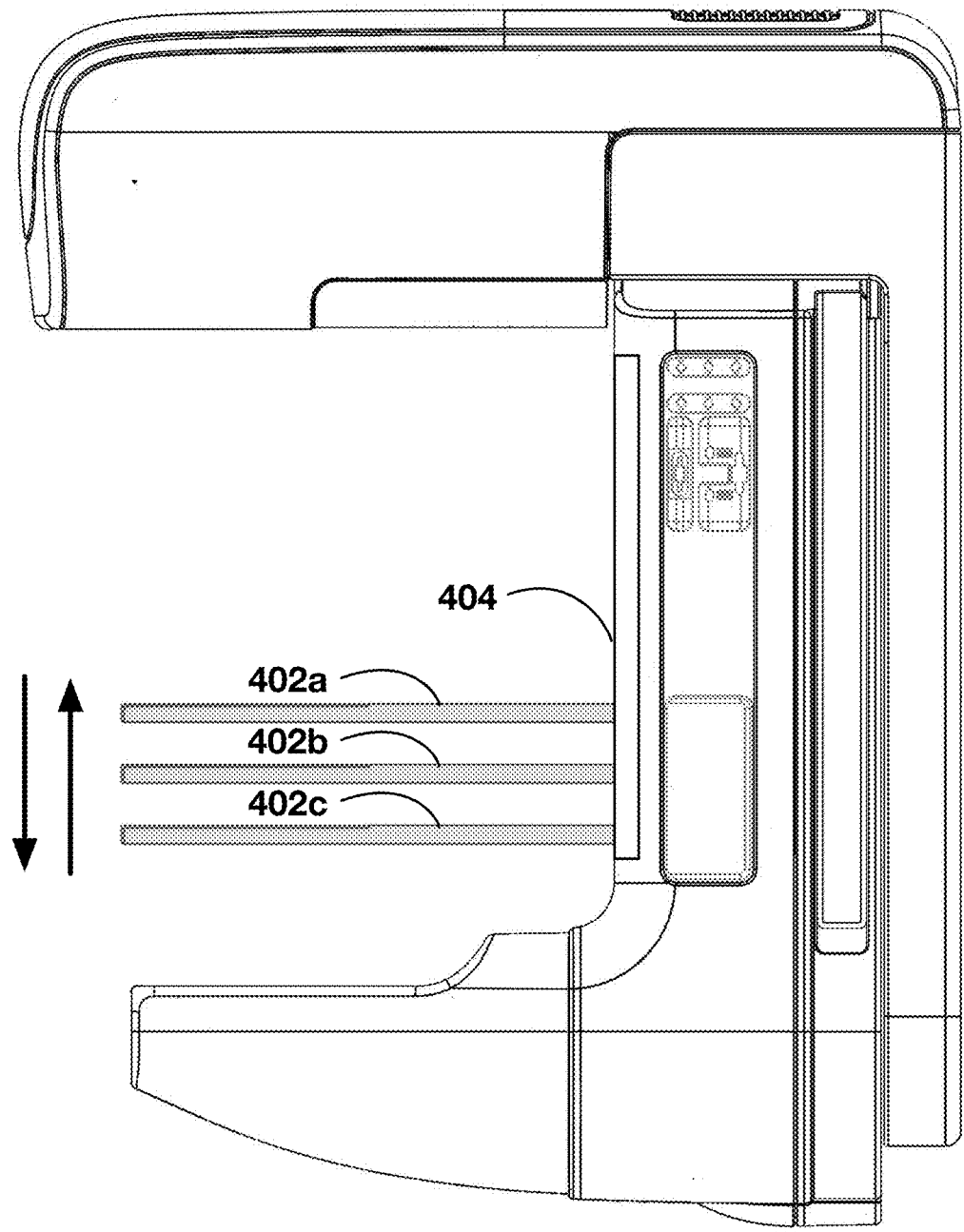
FIG. 4 illustrates an embodiment of an imaging system.

FIG. 4 illustrates an imaging system 400 according to an embodiment. As illustrated within FIG. 4, a magnification stand 402 may be deployed in a horizontal position. Magnification stand 402 may be vertically positioned in a plurality of positions 402a, 402b, and 402c. In some embodiments, at least one of positions 402a, 402b, and/or 402c may each correspond to a particular focal spot or magnification level. A vertical channel 404 integrated into the body of imaging system 400 may be used to guide magnification stand 402 to various vertical positions, and as described below, may be used to store magnification stand 402 when in a stowed position.

Figure 5:
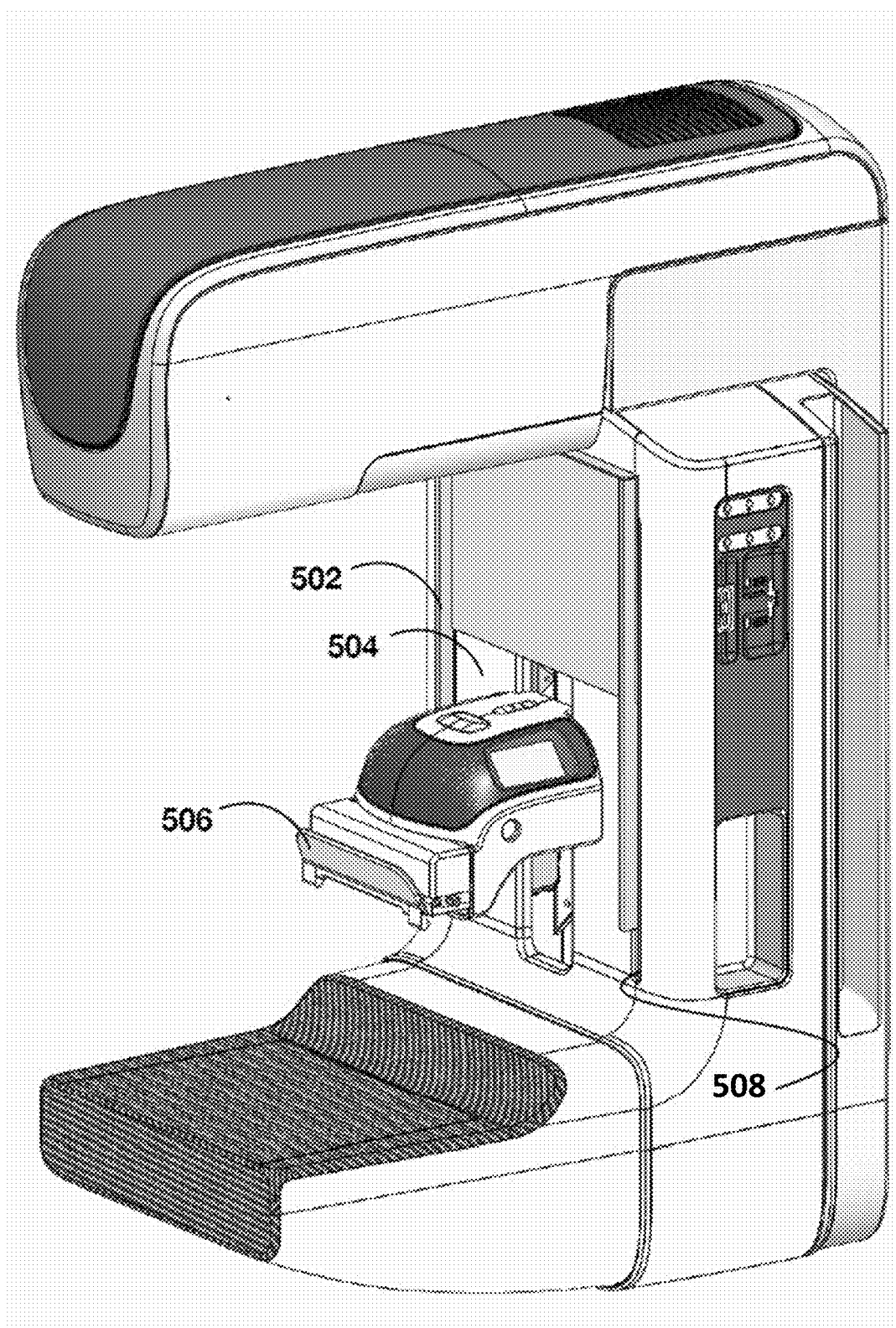
FIG. 5 illustrates an embodiment of an imaging system.

FIG. 5 illustrates an imaging system 500 according to an embodiment. As illustrated in FIG. 5, magnification stand 502 may include two arms connecting it to the body of imaging system 500, each with a separate hinge mechanism. In this embodiment, an opening 504 may be formed in a portion of the magnification stand closest to the body of imaging system 500 when in a horizontal deployed position. Opening 504 may be of a size to rotate around an attachment mechanism 506, which may be used to attach an accessory such as a face shield or compression paddle, in some embodiments. Vertical channel 508 may be used to guide the arms of magnification stand 502 into a plurality of vertical positions, as illustrated above in FIG. 4.

Figure 6:
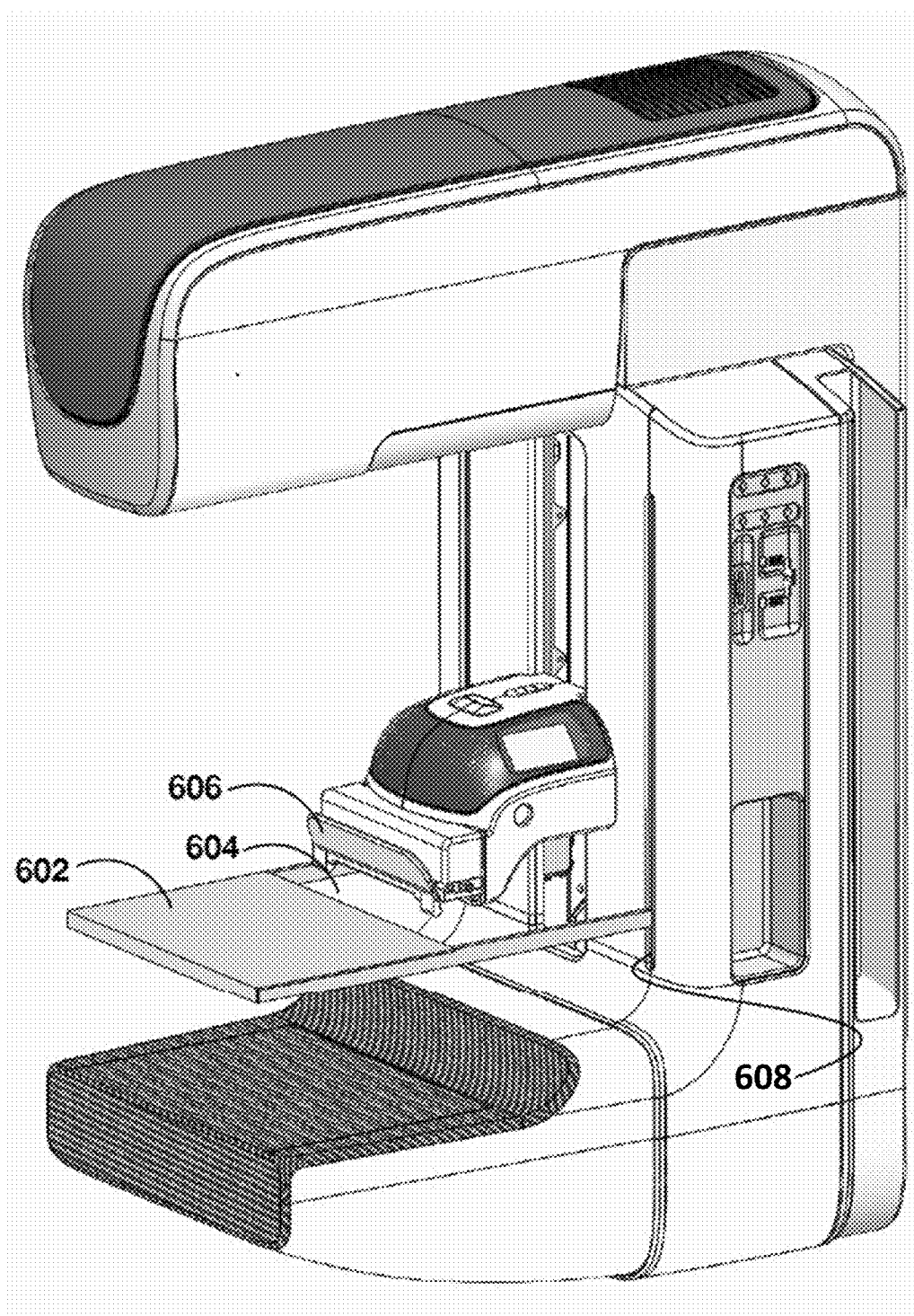
FIG. 6 illustrates an embodiment of an imaging system.

FIG. 6 illustrates an imaging system 600 according to an embodiment. As illustrated within FIG. 6, a magnification stand 602 may be deployed in a horizontal position. As described with respect to FIG. 5, two arms extending from magnification stand 602 to the body of imaging system 600 may form an opening 604 that allows magnification stand 602 to be deployed from a stowed position around an attachment mechanism 606 into a deployed position. Vertical channel 608 may be used to guide the arms of magnification stand 602 into a plurality of vertical positions, as illustrated above in FIG. 4.

Figure 7:
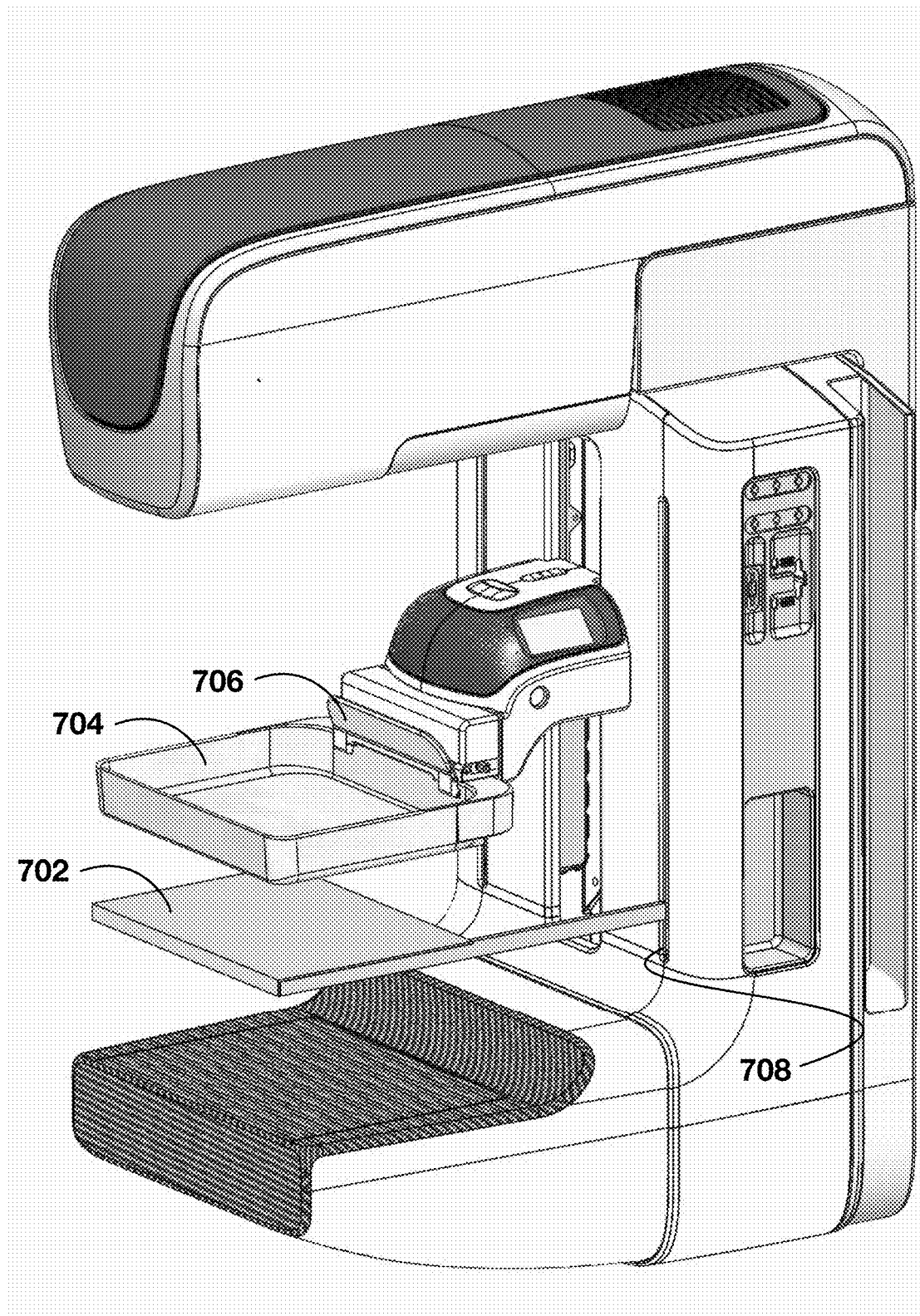
FIG. 7 illustrates an embodiment of an imaging system.

FIG. 7 illustrates an imaging system 700 according to an embodiment. As illustrated within FIG. 7, a magnification stand 702 may be deployed at a vertical position within vertical channel 708. Vertical channel 708 may be used to guide the arms of magnification stand 702 into a plurality of vertical positions, as illustrated above in FIG. 4. Also illustrated within FIG. 7 is a compression paddle 704, which may be attached to attachment mechanism 706 after magnification stand 702 has been deployed.

Figure 8:
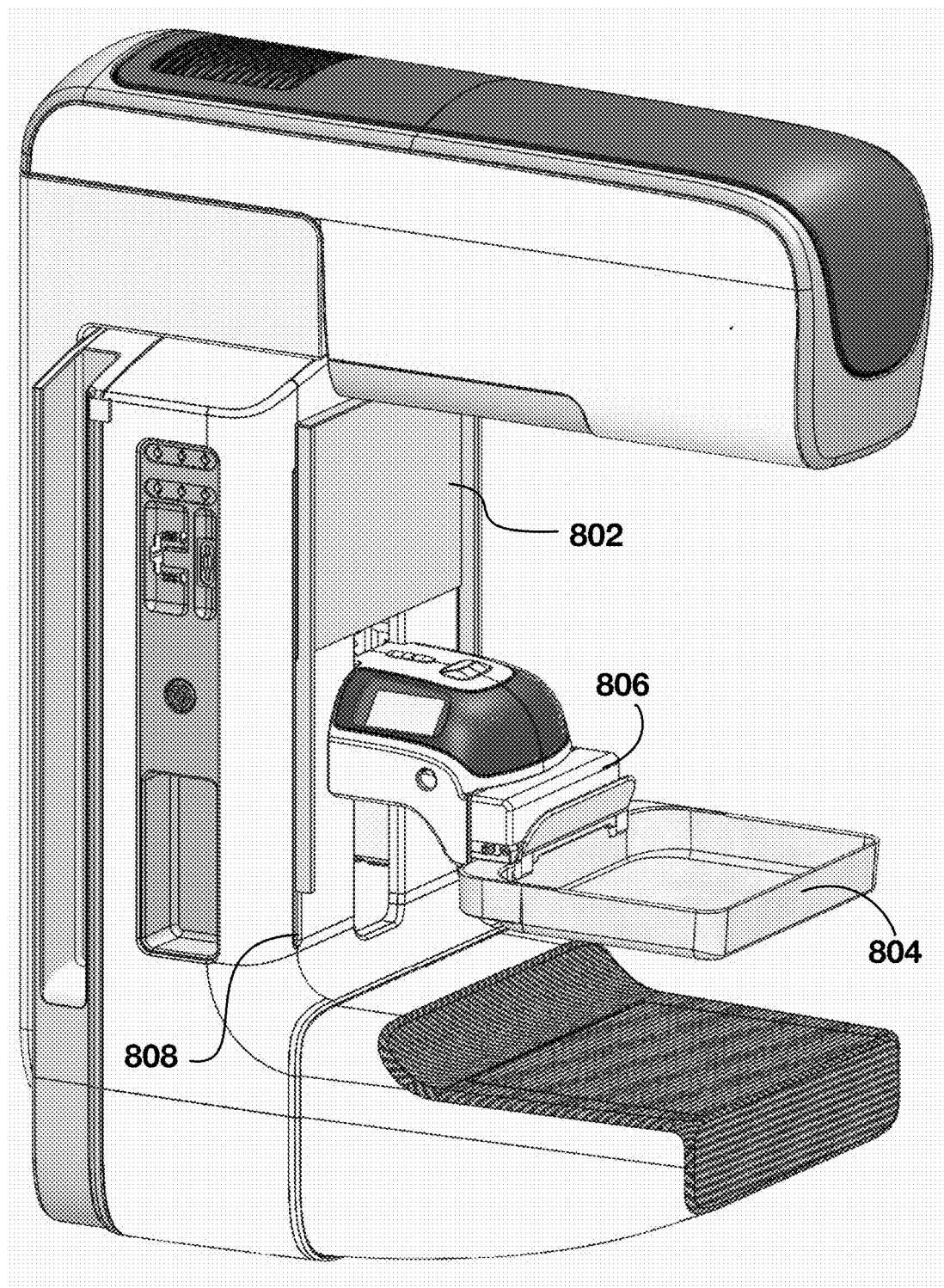
FIG. 8 illustrates an embodiment of an imaging system.

FIG. 8 illustrates an imaging system 800 according to an embodiment. As illustrated within FIG. 8, magnification stand 802 may be stowed partially within vertical channel 808. When stowed, a compression paddle 804 may be attached via attachment mechanism 806. It should be noted that, for magnification stand 802 to be deployed, compression paddle 804 would need to be first removed in this embodiment.

Figure 9:
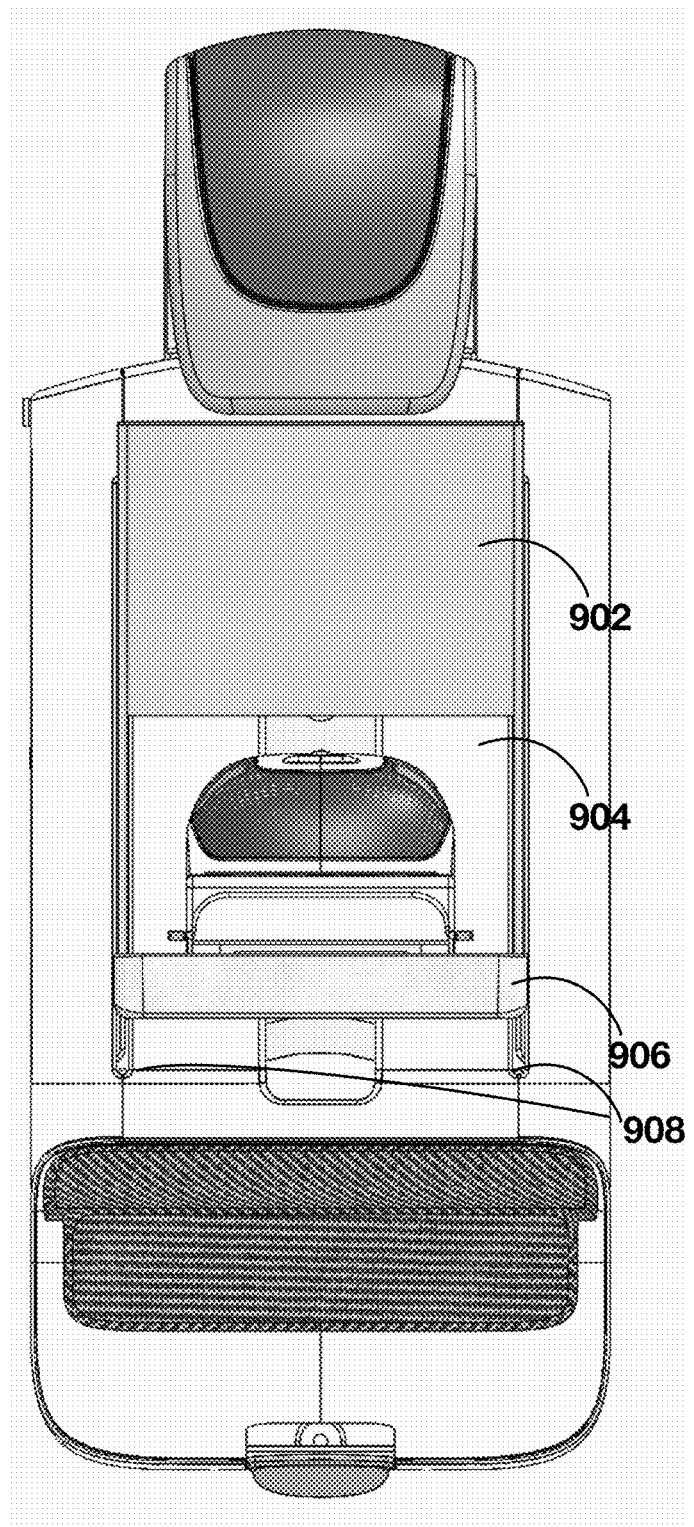
FIG. 9 illustrates an embodiment of an imaging system.

FIG. 9 illustrates an imaging system 900 according to an embodiment. As illustrated within FIG. 9, a magnification stand 902 may be placed in a stowed position. FIG. 9 clearly illustrates the size of opening 904, which allows for magnification stand to rotate around an attachment mechanism for compression paddle 906. Also illustrated are vertical channels 908, which may serve various purposes. For example, vertical channels 908 may be used to store at least a portion of magnification stand 902 when stowed. Further, vertical channels 908 may be used to guide a deployed magnification stand 902 into a plurality of vertical positions, each achieving a different focal spot or magnification level.

Included herein is a set of flow charts representative of exemplary methodologies for performing novel aspects of the disclosed architecture. While, for purposes of simplicity of explanation, the one or more methodologies shown herein, for example, in the form of a flow chart or flow diagram, are shown and described as a series of acts, it is to be understood and appreciated that the methodologies are not limited by the order of acts, as some acts may, in accordance therewith, occur in a different order and/or concurrently with other acts from that shown and described herein. For example, those skilled in the art will understand and appreciate that a methodology could alternatively be represented as a series of interrelated states or events, such as in a state diagram. Moreover, not all acts illustrated in a methodology may be required for a novel implementation.

Figure 10:
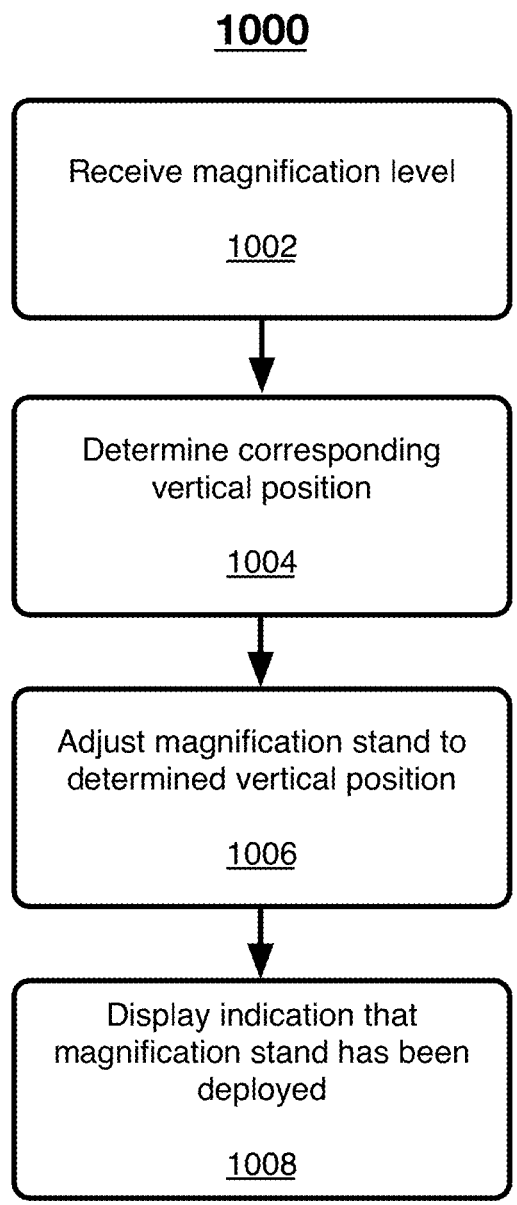
FIG. 10 illustrates a logic flow according to an embodiment.

FIG. 10 illustrates a logic flow 1000 according to an embodiment. The logic flow 1000 may be representative of some or all of the operations executed by one or more embodiments described herein, such as imaging systems 100-900, for example. Specifically, logic flow 1000 may illustrate operations performed by a position module, such as position module 114. In particular, logic flow 1000 may represent an embodiment in which an imaging system may automatically deploy a magnification stand based upon input to an interface by a practitioner.

At 1002, a selection of a magnification level may be received via an interface of an imaging system. As described herein, such an interface may include a GUI displayed on a display device, or may comprise one or more switches or buttons along with LEDs or other indicators. In some embodiments, a focal spot may be chosen instead of a magnification level, or a focal spot may be derived from a selected magnification level.

At 1004, a position module may use information stored within a position criteria database to determine a vertical position corresponding to the selected magnification level. As set forth above, a focal spot may be selected instead of a magnification level. In any event, a position module may correlate a selected magnification level or focal spot and determine a vertical position for a deployed magnification stand.

At 1006, a movement module, which may include a motor assembly described above, may be adjusted by a position module to the determined vertical position. At 1008, an interface of the imaging system may be used to display to a practitioner the status of the deployment and vertical positioning. The interface may include a GUI of a display device, which may indicate a successful deployment and indication of the vertical position, or corresponding magnification level or focal spot. In another embodiment, the interface may include one or more LED lights and/or other indicators to inform a practitioner that deployment is complete and an indication of the vertical position.

Figure 11:
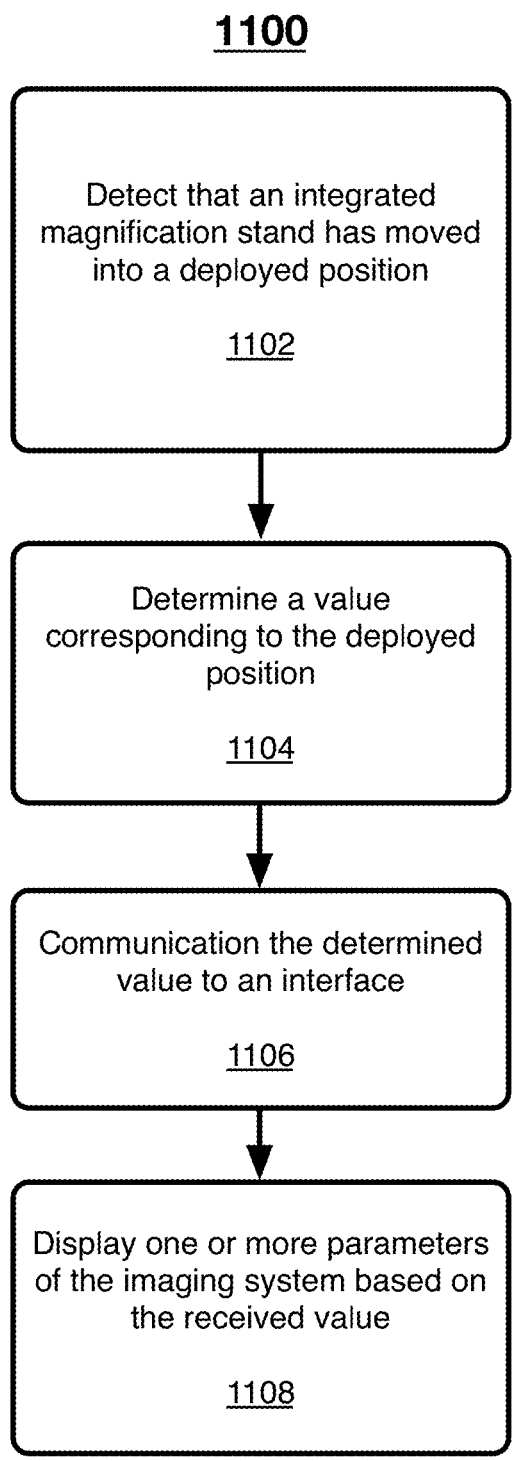
FIG. 11 illustrates a logic flow according to an embodiment.

FIG. 11 illustrates a logic flow 1100 according to an embodiment. Logic flow 1100 may be representative of some or all of the operations executed by one or more embodiments described herein, such as imaging systems 100-900, for example. Specifically, logic flow 1100 may illustrate operations performed by a position module, such as position module 114. In particular, logic flow 1100 may represent an embodiment in which a magnification stand is manually deployed by a practitioner, and a position module detects such deployment and communicates the detected deployment to an interface of an imaging system.

At 1102, a position sensor may detect that an integrated magnification stand has been moved into a deployed position. The position sensor may detect that the magnification stand has been deployed and/or a vertical position of the magnification stand.

At 1104, the position sensor may use information with a position criteria database to determine a value corresponding to the deployed position. For example, a position criteria database may correlate vertical positions of a magnifications stand with different magnification levels or focal spots.

At 1106, a position module may communicate the determined value to an interface of the imaging system, and at 1108, the interface may be configured to display one or more parameters of the imaging system based upon the received value. For example, a position module may determine a particular vertical position and determine that a certain focal spot has been achieved. The focal spot may be displayed to a practitioner in a GUI of a display, or via one or more labeled LED indicators of the imaging system. In this manner, a practitioner manually adjusting the magnification stand may be able to confirm that the physical position of the magnification stand corresponds to a desired parameter prior to an imaging procedure.

Figure 12:
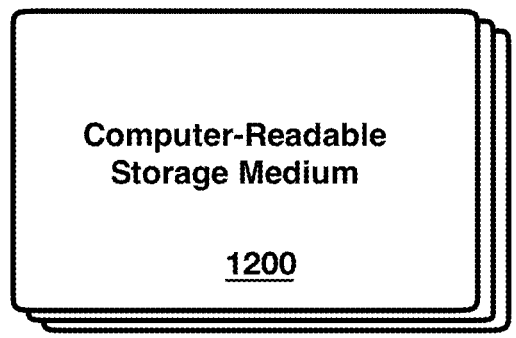
FIG. 12 illustrates an article of manufacture according to an embodiment.

FIG. 12 illustrates an article of manufacture according to an embodiment. Storage medium 1200 may comprise any computer-readable storage medium or machine-readable storage medium, such as an optical, magnetic or semiconductor storage medium. In some embodiments, storage medium 1200 may comprise a non-transitory storage medium. In various embodiments, storage medium 1200 may comprise an article of manufacture. In some embodiments, storage medium 1200 may store computer-executable instructions, such as computer-executable instructions to implement logic flow 1200, for example. Examples of a computer-readable storage medium or machine-readable storage medium may include any tangible media capable of storing electronic data, including volatile memory or non-volatile memory, removable or non-removable memory, erasable or non-erasable memory, writeable or re-writeable memory, and so forth. Examples of computer-executable instructions may include any suitable type of code, such as source code, compiled code, interpreted code, executable code, static code, dynamic code, object-oriented code, visual code, and the like. The embodiments are not limited to these examples.

Figure 13:
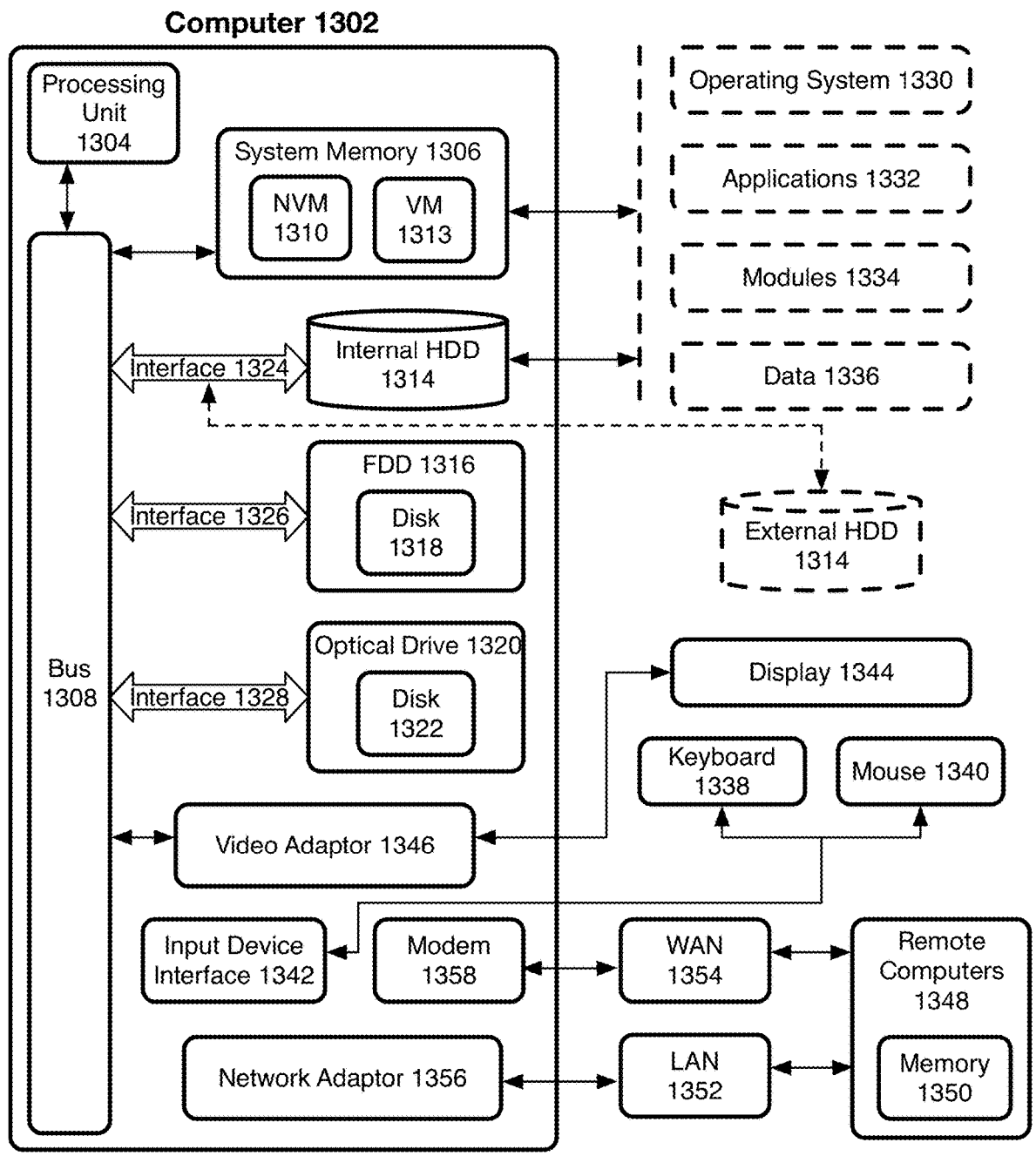
FIG. 13 illustrates an embodiment of a computing architecture.

FIG. 13 illustrates an embodiment of an exemplary computing architecture 1300 suitable for implementing various embodiments as previously described. In one embodiment, the computing architecture 1300 may comprise or be implemented as part of an electronic device. Examples of an electronic device may include those described herein. The embodiments are not limited in this context.

As used in this application, the terms "system" and "component" are intended to refer to a computer-related entity, either hardware, a combination of hardware and software, software, or software in execution, examples of which are provided by the exemplary computing architecture 1300. For example, a component can be, but is not limited to being, a process running on a processor, a processor, a hard disk drive, multiple storage drives (of optical and/or magnetic storage medium), an object, an executable, a thread of execution, a program, and/or a computer. By way of illustration, both an application running on a server and the server can be a component. One or more components can reside within a process and/or thread of execution, and a component can be localized on one computer and/or distributed between two or more computers. Further, components may be communicatively coupled to each other by various types of communications media to coordinate operations. The coordination may involve the uni-directional or bi-directional exchange of information. For instance, the components may communicate information in the form of signals communicated over the communications media. The information can be implemented as signals allocated to various signal lines. In such allocations, each message is a signal. Further embodiments, however, may alternatively employ data messages. Such data messages may be sent across various connections. Exemplary connections include parallel interfaces, serial interfaces, and bus interfaces.

The computing architecture 1300 includes various common computing elements, such as one or more processors, multi-core processors, co-processors, memory units, chipsets, controllers, peripherals, interfaces, oscillators, timing devices, video cards, audio cards, multimedia input/output (I/O) components, power supplies, and so forth. The embodiments, however, are not limited to implementation by the computing architecture 1500. As shown in FIG. 13, the computing architecture 1300 comprises a processing unit 1304, a system memory 1306 and a system bus 1308. Dual microprocessors, multi-core processors, and other multi-processor architectures may also be employed as the processing unit 1304.

The system bus 1308 provides an interface for system components including, but not limited to, the system memory 1306 to the processing unit 1304. The system bus 1208 can be any of several types of bus structure that may further interconnect to a memory bus (with or without a memory controller), a peripheral bus, and a local bus using any of a variety of commercially available bus architectures.

Interface adapters may connect to the system bus 1308 via a slot architecture, for example.

The computing architecture 1300 may comprise or implement various articles of manufacture. An article of manufacture may comprise a computer-readable storage medium to store logic, as described above with respect to FIG. 12.

The system memory 1306 may include various types of computer-readable storage media in the form of one or more higher speed memory units, such as read-only memory (ROM), random-access memory (RAM), dynamic RAM (DRAM), solid state memory devices (e.g., USB memory, solid state drives (SSD) and any other type of storage media suitable for storing information.). In the illustrated embodiment shown in FIG. 13, the system memory 1306 can include non-volatile memory 1310 and/or volatile memory 1313. A basic input/output system (BIOS) can be stored in the non-volatile memory 1310.

The computer 1302 may include various types of computer-readable storage media in the form of one or more lower speed memory units, including an internal (or external) hard disk drive (HDD) 1314, a magnetic floppy disk drive (FDD) 1316 to read from or write to a removable magnetic disk 1318, and an optical disk drive 1320 to read from or write to a removable optical disk 1322 (e.g., a CD-ROM, DVD, or Blu-ray). The HDD 1314, FDD 1316 and optical disk drive 1320 can be connected to the system bus 1308 by a HDD interface 1324, an FDD interface 1326 and an optical drive interface 1328, respectively. The HDD interface 1324 for external drive implementations can include at least one or both of Universal Serial Bus (USB) and IEEE 1394 interface technologies.

The drives and associated computer-readable media provide volatile and/or nonvolatile storage of data, data structures, computer-executable instructions, and so forth. For example, a number of program modules can be stored in the drives and memory units 1310, 1313, including an operating system 1330, one or more application programs 1332, other program modules 1334, and program data 1336. In one embodiment, the one or more application programs 1332, other program modules 1334, and program data 1336 can include, for example, the various applications and/or components to implement the disclosed embodiments.

A user can enter commands and information into the computer 1302 through one or more wire/wireless input devices, for example, a keyboard 1338 and a pointing device, such as a mouse 1340. Other input devices may include microphones, infra-red (IR) remote controls, radio-frequency (RF) remote controls, game pads, stylus pens, card readers, dongles, finger print readers, gloves, graphics tablets, joysticks, keyboards, retina readers, touch screens (e.g., capacitive, resistive, etc.), trackballs, trackpads, sensors, styluses, and the like. These and other input devices are often connected to the processing unit 1304 through an input device interface 1342 that is coupled to the system bus 1308, but can be connected by other interfaces such as a parallel port, IEEE 1394 serial port, a game port, a USB port, an IR interface, and so forth.

A display 1344 is also connected to the system bus 1308 via an interface, such as a video adaptor 1346. The display 1344 may be internal or external to the computer 1302. In addition to the display 1344, a computer typically includes other peripheral output devices, such as speakers, printers, and so forth.

The computer 1302 may operate in a networked environment using logical connections via wire and/or wireless communications to one or more remote computers, such as a remote computer 1348. The remote computer 1348 can be a workstation, a server computer, a router, a personal computer, portable computer, microprocessor-based entertainment appliance, a peer device or other common network node, and typically includes many or all of the elements described relative to the computer 1302, although, for purposes of brevity, only a memory/storage device 1350 is illustrated. The logical connections depicted include wire/wireless connectivity to a local area network (LAN) 1352 and/or larger networks, for example, a wide area network (WAN) 1354. Such LAN and WAN networking environments are commonplace in offices and companies, and facilitate enterprise-wide computer networks, such as intranets, all of which may connect to a global communications network, for example, the Internet.

When used in a LAN networking environment, the computer 1302 is connected to the LAN 1352 through a wire and/or wireless communication network interface or adaptor 1356. The adaptor 1356 can facilitate wire and/or wireless communications to the LAN 1352, which may also include a wireless access point disposed thereon for communicating with the wireless functionality of the adaptor 1356.

When used in a WAN networking environment, the computer 1302 can include a modem 1358, or is connected to a communications server on the WAN 1354, or has other means for establishing communications over the WAN 1354, such as by way of the Internet. The modem 1358, which can be internal or external and a wire and/or wireless device, connects to the system bus 1308 via the input device interface 1342. In a networked environment, program modules depicted relative to the computer 1302, or portions thereof, can be stored in the remote memory/storage device 1350. It will be appreciated that the network connections shown are exemplary and other means of establishing a communications link between the computers can be used.

The computer 1302 is operable to communicate with wire and wireless devices or entities using the IEEE 802 family of standards, such as wireless devices operatively disposed in wireless communication (e.g., IEEE 802.11 over-the-air modulation techniques). This includes at least Wi-Fi (or Wireless Fidelity), WiMax, and Bluetooth™ wireless technologies, among others.

Some embodiments may be described using the expression "one embodiment" or "an embodiment" along with their derivatives. These terms mean that a particular feature, structure, or characteristic described in connection with the embodiment is included in at least one embodiment. The appearances of the phrase "in one embodiment" in various places in the specification are not necessarily all referring to the same embodiment. Further, some embodiments may be described using the expression "coupled" and "connected" along with their derivatives. These terms are not necessarily intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

A procedure is here, and generally, conceived to be a self-consistent sequence of operations leading to a desired result. These operations are those requiring physical manipulations of physical quantities. Usually, though not necessarily, these quantities take the form of electrical, magnetic or optical signals capable of being stored, transferred, combined, compared, and otherwise manipulated. It proves convenient at times, principally for reasons of common usage, to refer to these signals as bits, values, elements, symbols, characters, terms, numbers, or the like. It should be noted, however, that all of these and similar terms are to be associated with the appropriate physical quantities and are merely convenient labels applied to those quantities.

Further, the manipulations performed are often referred to in terms, such as adding or comparing, which are commonly associated with mental operations performed by a human operator. No such capability of a human operator is necessary, or desirable in most cases, in any of the operations described herein which form part of one or more embodiments. Rather, the operations are machine operations. Useful machines for performing operations of various embodiments include general purpose digital computers or similar devices.

Various embodiments also relate to apparatus or systems for performing these operations. This apparatus may be specially constructed for the required purpose or it may comprise a general-purpose computer as selectively activated or reconfigured by a computer program stored in the computer. The procedures presented herein are not inherently related to a particular computer or other apparatus. Various general-purpose machines may be used with programs written in accordance with the teachings herein, or it may prove convenient to construct more specialized apparatus to perform the required method steps. The required structure for a variety of these machines will appear from the description given.

The following include non-limiting example embodiments:

Example 1 is an imaging system, comprising an imaging detector to capture an image of human tissue, a compression paddle situated apart from the imaging detector, and a magnification stand configured to rotate between a first position and a second position, wherein the magnification stand is situated between the compression paddle and the imaging detector in the first position such that the human tissue can be compressed between the magnification stand and the compression paddle, and wherein the magnification stand is rotated to the second position in which the second position is generally perpendicular to the first position.

Example 2 is the imaging system of Example 1, further comprising a position sensor configured to detect a position of the magnification stand.

Example 3 is the imaging system of Example 2, further comprising a processing circuit to configure a graphical user interface of the imaging system based upon a position detected by the position sensor.

Example 4 is the imaging system of any of Examples 1-3, further comprising an input mechanism configured to receive a position selection a movement module configured to adjust the magnification stand based upon the received position.

Example 5 is the imaging system of Example 4, wherein the input mechanism is a graphical user interface on a display device.

Example 6 is the imaging system of Example 4, wherein the input mechanism is a switch or button.

Example 7 is the imaging system of any of Examples 4-6, wherein the received position corresponds to a focal spot.

Example 8 is the imaging system of any of Examples 1-7, further comprising a sliding mechanism configured to adjust the magnification stand in the first position upwards and downwards into a plurality of vertical positions.

Example 9 is the imaging system of any of Examples 1-8, further comprising an attachment mechanism positioned above the magnification stand when in the first position.

Example 10 is the imaging system of Example 9, wherein the magnification stand includes an opening between two opposite arms that allows the magnification stand to rotate around the attachment mechanism, via the hinge, from the first position to the second position.

Example 11 is a computer-implemented method for deployment of an integrated magnification stand, comprising receiving, via an interface of an imaging system, a selection of a magnification level, determining, by a position module, a vertical position corresponding to the selected magnification level, adjusting, by a movement module, the magnification stand into a deployed position at the determined vertical position, and displaying, via the interface of the imaging system, an indication that the magnification stand has been deployed.

Example 12 is the computer-implemented method of Example 11, wherein the interface comprises a graphical user interface of a display device connected to the imaging system.

Example 13 is the computer-implemented method of Example 12, wherein the graphical user interface includes a plurality of magnification levels, each corresponding to a different vertical position for the magnification stand.

Example 14 is the computer-implemented method of any of Examples 11-13, wherein the interface comprises one or more switches and LED indicators.

Example 15 is the computer-implemented method of any of Examples 11-14, wherein the selected magnification level corresponds to a focal spot.

Example 16 is a computer-implemented method for position detection in an imaging system, the method comprising detecting, by a position sensor, that an integrated magnification stand has been moved into a deployed position, determining, by the position sensor, a value corresponding to the deployed position, communicating, by the position sensor, the determined value to an interface of the imaging system, and displaying, by the interface, one or more parameters of the imaging system based upon the received value.

Example 17 is the computer-implemented method of Example 16, wherein the value corresponding to the deployed position including a vertical position.

Example 18 is the computer-implemented method of Example 17, wherein the vertical position corresponds to a focal point.

Example 19 is the computer-implemented method of any of Examples 16-18, wherein the interface comprises a graphical user interface of a display device connected to the imaging system.

Example 20 is the computer-implemented method of any of Examples 16-19, wherein the interface comprises one or more switches and LED indicators In the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment. In the appended claims, the terms "including" and "in which" are used as the plain-English equivalents of the respective terms "comprising" and "wherein," respectively. Moreover, the terms "first," "second," "third," and so forth, are used merely as labels, and are not intended to impose numerical requirements on their objects.

What has been described above includes examples of the disclosed architecture. It is, of course, not possible to describe every conceivable combination of components and/or methodologies, but one of ordinary skill in the art may recognize that many further combinations and permutations are possible.

The invention claimed is:

1. An imaging system, comprising:
   an imaging system body;
   an imaging detector disposed within the imaging system body to capture an image of human tissue;
   a paddle movable relative to the imaging system body and situated apart from the imaging detector;
   a magnification stand configured to rotate between a first position and a second position, wherein the magnification stand is situated between the compression paddle and the imaging detector in the first position such that the human tissue is compressed between the magnification stand and the compression paddle, and wherein the magnification stand is rotated to the second position in which the second position is generally perpendicular to the first position; and
   an attachment mechanism for securing detachably securing the compression paddle to the imaging system body, wherein the attachment mechanism is positioned above the magnification stand when in the first position, and wherein the magnification stand defines an opening between two opposite arms that allows the magnification stand to rotate around the attachment mechanism, from the first position to the second position.

2. The imaging system of claim 1, further comprising a position sensor configured to detect a position of the magnification stand.

3. The imaging system of claim 2, further comprising a processing circuit to configure a graphical user interface of the imaging system based upon a position detected by the position sensor.

4. The imaging system of claim 1, further comprising:
   an input mechanism configured to receive a position selection
   a movement module configured to adjust the magnification stand based upon the received position.

5. The imaging system of claim 4, wherein the input mechanism is a graphical user interface on a display device.

6. The imaging system of claim 4, wherein the input mechanism is a switch or button.

7. The imaging system of claim 4, wherein the received position corresponds to a focal spot.

8. The imaging system of claim 1, further comprising a sliding mechanism configured to adjust the magnification stand in the first position upwards and downwards into a plurality of vertical positions.

9. The imaging system of claim 1, wherein the magnification stand is configured to rotate around the attachment mechanism, via a hinge, from the first position to the second position.

10. A computer-implemented method for deployment of an integrated magnification stand, comprising:
    receiving, via an interface of an imaging system, a selection of a magnification level;
    determining, by a position module, a vertical position corresponding to the selected magnification level;
    adjusting, by a movement module, the magnification stand into a deployed position at the determined vertical position, wherein adjusting the magnification stand into the deployed position comprises rotating the magnification stand to the deployed position from a position substantially perpendicular to the deployed position; and
    displaying, via the interface of the imaging system, an indication that the magnification stand has been deployed.

11. The computer-implemented method of claim 10, wherein the interface comprises a graphical user interface of a display device connected to the imaging system.

12. The computer-implemented method of claim 11, wherein the graphical user interface includes a plurality of magnification levels, each corresponding to a different vertical position for the magnification stand.

13. The computer-implemented method of claim 10, wherein the interface comprises one or more switches and LED indicators.

14. The computer-implemented method of claim 10, wherein the selected magnification level corresponds to a focal spot.

15. A computer-implemented method for position detection in an imaging system, the method comprising:
    detecting, by a position sensor, that an integrated magnification stand has been moved into a deployed position from a position substantially perpendicular to the deployed position;
    determining, by the position sensor, a value corresponding to the deployed position;
    communicating, by the position sensor, the determined value to an interface of the imaging system; and
    displaying, by the interface, one or more parameters of the imaging system based upon the received value.

16. The computer-implemented method of claim 15, wherein the value corresponding to the deployed position including a vertical position.

17. The computer-implemented method of claim 16, wherein the vertical position corresponds to a focal point.

18. The computer-implemented method of claim 15, wherein the interface comprises a graphical user interface of a display device connected to the imaging system.

19. The computer-implemented method of claim 15, wherein the interface comprises one or more switches and LED indicators.

* * * * *